(12) United States Patent
Sjong (10) Patent No.: US 8,437,965 B2
(45) Date of Patent: May 7, 2013

(54) SENSING CHEMICALS IN AQUEOUS ENVIRONMENTS

(75) Inventor: Angele Sjong, Louisville, CO (US)

(73) Assignee: Empire Technology Development LLC, Wilmington, DE (US)

( * ) Notice: Subject to any disclaimer, the term of this patent is extended or adjusted under 35 U.S.C. 154(b) by 723 days.

(21) Appl. No.: 12/715,373

(22) Filed: Mar. 1, 2010

(65) Prior Publication Data

US 2011/0213565 A1 Sep. 1, 2011

(51) Int. Cl.
*G01N 31/00* (2006.01)

(52) U.S. Cl.
USPC .......................................................... 702/23

(58) Field of Classification Search .................. 702/22, 702/23, 182–185
See application file for complete search history.

(56) References Cited

U.S. PATENT DOCUMENTS

| 7,204,971 B2 | 4/2007 | Sandhage | |
| 8,355,136 B2 * | 1/2013 | Glazier et al. | 356/445 |
| 2008/0038170 A1 | 2/2008 | Sandhage et al. | |
| 2009/0221014 A1 * | 9/2009 | Reardon et al. | 435/18 |

OTHER PUBLICATIONS

De, Stefano, et al., "Highly sensitive optochemical gas detection by luminescent marine diatoms," Appl. Phys. Lett., Aug. 2007, 3 pgs, vol. 91, Document No. 051921, American Institute of Physics, USA.
Jackusch, M., et al., "Selective Polymer Materials: Absolute Determination of Their Sorption Properties," Advanced Environmental and Chemical Sensing Technology, Proc. SPIE, Feb. 2001, p. 93-98, vol. 4205, Bellingham, Washington, USA.
Lettieri, et al., "The Gas-Detection Properties of Light-Emitting Diatoms", Adv. Funct. Mater., 2008, pp. 1257-1264, vol. 18, Wiley-VCH, Germany.
King, et al., "Optical-Fiber-Mounted Porous Silicon Photonic Crystals for Sensing Organic Vapor Breakthrough in Activated Carbon", Adv. Mater., 2007, pp. 4530-4534, vol. 19, Wiley-VCH, Germany.
Gordon, et al., "The Glass Menagerie: diatoms for novel applications in nanotechnology", Trends in Biotech., 2008, pp. 116-127, vol. 27, No. 2, Elsevier.
Setaro, et al., "Highly sensitive optochemical gas detection by luminescent marine diatoms", Appl. Phys. Lett., 2007, pp. 051921-1 to 051921-3, vol. 91, American Institute of Physics, USA.
Collino, et al., "Thin Films of Functionalized Amorphous Silica for Immunosensors Application", J. of Sol-Gel Science and Tech., 1994, pp. 823-826, vol. 2, Kluwer Academic Publishers, USA/The Netherlands.
Losic, et al., "Diatomaceous Lessons in Nanotechnology and Advanced Materials", Adv. Mater., 2009, pp. 2947-2958, vol. 21, Wiley-VCH, Germany.

(Continued)

*Primary Examiner* — Edward Raymond
(74) *Attorney, Agent, or Firm* — Pepper Hamilton LLP (57) ABSTRACT

Techniques for sensing chemicals in aqueous environments, and systems configured for sensing chemicals in aqueous environments are provided. More particularly, techniques and systems for detecting a presence or absence of aromatic chemicals in aqueous environments are provided. An example may include receiving emitted light from a first port of an optical circulator, reflecting at least a portion of the received emitted light to produce reflected light, and transmitting the reflected light from the second port of the optical circulator. The reflected light may be produced, at least in part, by an interaction of chemicals and an array of photonic silica of the second port.

22 Claims, 5 Drawing Sheets

OTHER PUBLICATIONS

International Search Report with Written Opinion in PCT/US2010/053663 issued on Dec. 15, 2010 by the Australian Patent Office.

Peach, et al., On the culture of the marine diatom nitzschia closeterium (F.) minutissima, in artificial sea-water, Biochem Journal, 1924, pp. 464-468, University of London, United Kingdom.

Wisely, et al., A culture method for marine diatoms and flagellates, Tuatara, 1963, 9 pp., vol. 11, Issue 1, C.S.I.R.O. Marine Laboratory, Australia.

Wang, et al., Studies on culture conditions of benthic diatoms for feeding abalone, Chinese Journal of Oceanology and Limnology, 1999, pp. 105-111, vol. 17, No. 2, China.

De Stefano, et al., "Marine diatoms as optical chemical sensors", Applied Physics Letters, 2005, pp. 233902-1 to 233902-3, vol. 87, USA.

De Stefano, et al., "Optical characterisation of biological nano-porous silica structures", Proc. of SPIE, 2005, pp. 59250S-1 to 59250S-5, vol. 5925, USA.

Townley, H.E. et al., Modification of the physical and optical properties of the frustules of the diatom *Coscinodiscus wailesii* by nickel sulfate, Nanotechnology, 2007, 5 pp., vol. 18 (295101), UK.

Umemura, et al., Controlled nanoporous structures of a marine diatom. J. Nanosci. Nanotechnol., 2007, pp. 2842-2846, vol. 7, American Scientific Publishers, USA.

Umemura, et al., Regulated growth of diatom cells on self-assembled monolayers, J. of Nanobiotechnol., 2007, 14 pp., vol. 5, Issue 2, USA.

Bismuto, et al., Marine diatoms as optical chemical sensors: A time-resolved study, Sensors and Actuators, 2008, pp. 396-399, B 130, Elsevier.

Jeffryes, et al., Electroluminescence and Photoluminescence from Nanostructured Diatom Frustules Containing Metabolically Inserted Germanium, Adv. Mater., 2008, pp. 2633-2637, vol. 20, Wiley-VCH, Germany.

Jeffryes, et al., Two-stage photobioreactor process for the metabolic insertion of nanostructured germanium into the silica microstructure of the diatom Pinnularia sp., Mater. Sci. Engin. C, 2008, pp. 107-118, vol. 28, Elsevier.

Qin, et al., Biological Fabrication of Photoluminescent Nanocomb Structures by Metabolic Incorporation of Germanium into the Biosilica of the Diatom Nitzschia Frustulum, ACS Nano, 2008, pp. 1296-1304, vol. 2, No. 6, American Chemical Society, USA.

Umemura, et al., Diatom Cells Grown and Baked on a Functionalized Mica Surface, J. Biol. Phys., 2008, pp. 189-196, vol. 34, Springer Science, Germany.

De Stefano, et al., "Marine diatoms as optical biosensors", Biosensors and Bioelectronics, 2009, pp. 1580-1584, vol. 24, Elsevier.

http://en.wikipedia.org/wiki/Diatom—date retrieved Jan. 14, 2011.
http://en.wikipedia.org/wiki/Frustule—date retrieved Jan. 14, 2011.
http://en.wikipedia.org/wiki/ Optical circulator—date retrieved Jan. 14, 2011.

* cited by examiner

400 A computer program product

402 A signal bearing medium

404 At least one of one or more computer-readable instructions configured to:

receive a signal representative of one of more of an intensity of light, a wavelength of the light and/or a frequency of the light compare at least a portion of the signal representative of one or more of the intensity, the wavelength and/or the frequency of the light with aromatic chemical information stored in one or more aromatic chemical databases detect one or more of the presence and/or absence of the one or more aromatic chemicals based, at least in part, on the comparing of at least a portion of the signal representative of the intensity, the wavelength and/or the frequency of the light with the aromatic chemical information stored in the one or more aromatic databases

| 406 a computer-readable medium | 408 a recordable medium | 410 a communications medium |

SENSING CHEMICALS IN AQUEOUS ENVIRONMENTS

BACKGROUND

The present disclosure is related to sensing chemicals in aqueous environments and, more particularly, to detecting a presence or absence of aromatic chemicals in aqueous environments.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

This disclosure is drawn, inter alia, to methods, systems, devices, and/or apparatus related to sensing chemicals in aqueous environments and, more particularly, to detecting a presence or absence of aromatic chemicals in aqueous environments.

The present disclosure contemplates that existing analytical methods (e.g., gas chromatography and/or mass spectrometry) for analyzing for chemical contamination in aqueous environments may be expensive and/or labor-intensive. In addition, analysis results may be delayed by days or weeks after a sampling event occurs. Such delays may not allow for immediate feedback and/or real-time monitoring of chemical contaminants. Some analytical methods may include large networks of various sensors to identify and/or analyze chemical contamination. However, such large networks of sensors may be limited to oxygen and nitrate monitoring systems. These analytical methods may not offer real-time monitoring of known chemicals (e.g., organic solvents) in aqueous systems and environments, particularly near effluent discharge points and aquifers located beneath storage tanks (including underground or above ground tanks).

The present disclosure contemplates that sensors for monitoring volatile organic chemicals (or aromatic chemicals) in effluents, aquifers, bodies of water and/or other aqueous environments may be constructed using an array of photonic silica frustules from cultured diatoms. In some example embodiments, the present disclosure describes methods for monitoring chemicals in industrial effluents when the identities of the chemicals of concern may be known and the solvents may be nucleophilic (e.g., xylene, toluene, benzene, ethylbenzene, pyridine and/or alcohols). Example embodiments (or portions thereof) may be implemented in and/or near effluents, aquifers, bodies of water and/or other aqueous environments. In some embodiments, sensors may be at least partially in contact with effluents, aquifers, bodies of water and/or other aqueous environments associated with and/or comprising aromatic chemicals. In some embodiments, only a portion (e.g., an array of photonic silica) of the sensing system may be in contact with effluents, aquifers, bodies of water and/or other aqueous environments associated with and/or comprising aromatic chemicals.

An optical circulator may be described as a three-port device (including port 1, port 2 and port 3, for example) that may allow light to travel in one direction: from port 1 to port 2, and then from port 2 to port 3. In an example optical circulator, light emitted from port 2 that is reflected in any direction may be directed on to port 3. Optical circulators may be used in advanced communication systems and fiber-optic sensor applications, for example.

Figure 1:
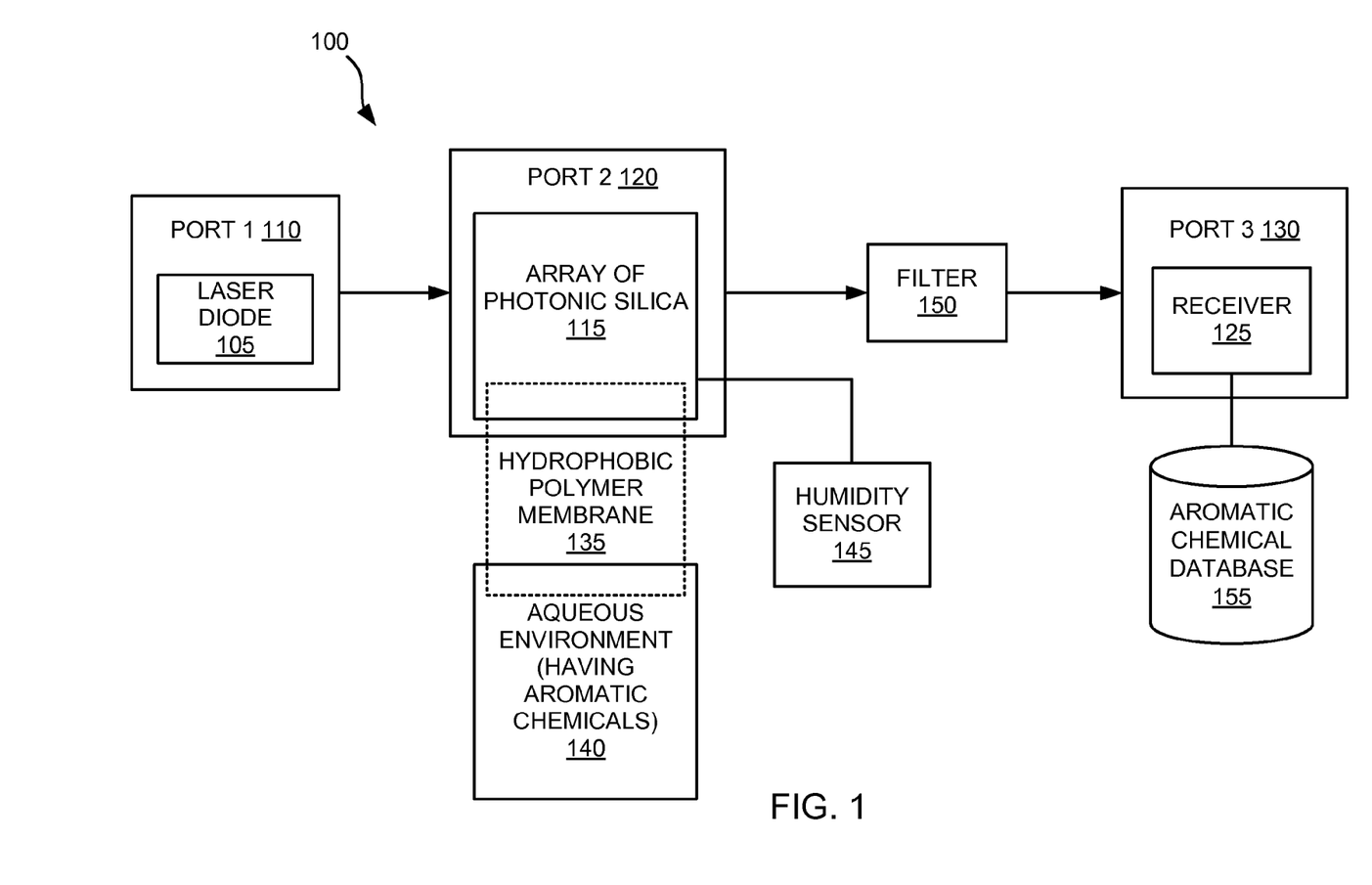
FIG. 1 is a block diagram illustrating some example systems for sensing aromatic chemicals.

FIG. 1 is a block diagram illustrating some example systems for sensing aromatic chemicals, arranged in accordance with at least some embodiments of the present disclosure. In some examples, an optical circulator 100 may comprise a Port 1 110, a Port 2 120 and a Port 3 130. Port 1 110 may comprise a laser diode configured to produce emitted light. Port 2 120 may comprise an array of photonic silica 115 having a plurality of frustules. The array of photonic silica 115 may be configured to receive the emitted light and reflect at least a portion of the emitted light as reflected light. The reflected light may be determined, at least in part, by an interaction of the aromatic chemicals and the plurality of frustules. Port 3 130 may comprise a receiver configured to receive and capture at least a portion of the reflected light.

In the described examples, Port 1 110, Port 2 120 and/or Port 3 130 may represent abstract stages of the presently disclosed subject matter, and may not be limited to optical circulators. Specifically, Port 1 110 may correspond to a light transmitting stage, Port 2 120 may correspond to a light hosting stage (where, for example, an array of photonic silica may reside), and Port 3 130 may correspond to a light receiving or collecting stage.

As depicted in FIG. 1, a light emitting device, such as a laser diode 105, located in Port 1 110, may be configured to transmit light to Port 2 120. Laser diode 105 may have a wavelength in the range of approximately 300 nanometers (nm) to approximately 400 nm, and may comprise an Indium Gallium Aluminum Arsenide (InGaAlAs) diode, an Indium Gallium Arsenide Phosphate (InGaAsP) diode and/or or a Gallium Arsenide (GaAs) diode. Other lasers with different wavelengths and chemical properties may also be used in some example embodiments. In some examples, the laser diode may be adapted to emit light to yield a desired photoluminescence from the array of photonic silica.

In some examples, Port 2 120 may comprise an array of photonic silica 115. An example array of photonic silica 115, may be arranged into a matrix of N by M dimensions, with anywhere from 1 to P layers in thickness (where N, M and P may be any numeral). In some examples, the array of photonic silica 115 may be cultured or arranged from diatoms and/or a diatomic material. An external part of the diatoms, or frustules, may be isolated as the material that may comprise the array of photonic silica 115. In some examples, frustules may self assemble into the aforementioned matrix.

The array of photonic silica 115 may be implemented in conjunction with a hydrophobic polymer membrane 135 that may substantially enrich the concentration of aromatic chemicals 140 in an aqueous environment. The hydrophobic polymer membrane 135 may serve as a mechanism to concentrate aromatic chemicals 140 onto the array of photonic silica 115. The hydrophobic polymer membrane 135 may protect the array of photonic silica 115 from being penetrated by water, while allowing aromatic chemicals 140 to pass through. Thus, the aromatic chemicals 140 may permeate the hydrophobic polymer membrane 135 and reach the array of photonic silica 115. Upon reaching the array of photonic silica 115, the aromatic chemicals 140 may alter the array of photonic silica's 115 sensitivity to light. In some examples, the polymer membrane 135 may surround and/or encase the array of photonic silica 115 when the array of photonic silica 115 is placed in an aqueous environment. This may allow easier detection of the presence or absence of aromatic chemicals 140. Hydrophobic polymer membrane 135 may comprise poly(ethylene-co-propylene), poly(acrylonitrile-co-butadiene), silicones, plasticized PVC, butadiene copolymers and/or fluoropolymer materials, among others.

In some examples, when the laser diode 105 emits light that hits the array of photonic silica 115, the aromatic chemicals 140 that may subsist on and/or around the array of photonic silica 115 may cause the emitted light from the laser diode 105 to be reflected. In some examples, the reflected light may comprise light with a wavelength in a range from about 300 nm to about 700 nm. As a result of the interaction of the aromatic chemicals 140 with the array of photonic silica 115, such reflection may be more enhanced than it may otherwise be.

In general, photoluminescence may be a process in which a substance absorbs photons (e.g., electromagnetic radiation) and, in turn, radiates photons. Photoluminescence of the array of photonic silica 115 may be a function of the properties (such as the frustules' pore size, for example) of the frustules. In some examples, a predetermined chemical substance (e.g., nickel sulfate) may be used to alter the size of frustule pores. For example, altering the frustules' pore size may include making the pores either larger or smaller, depending on the type of aromatic chemicals 140 to be detected. Some aromatic chemicals may yield greater photoluminescence at certain pore size(s) than other aromatic chemicals. Example aromatic chemicals 140 may include xylene, toluene, benzene, ethylbenzene, pyridine, alcohol, tetrachloroethane, or chlorobenzene, among others.

In some examples, environmental humidity may shift the wavelength (and, in turn, the frequency) for which a peak amplitude of photoluminescence may be observed. A humidity sensor 145 may be coupled to the array of photonic silica 115 so that the humidity sensor 145 may detect the amount of humidity. This configuration may assist in predicting the wavelength shift caused by humidity levels. The system 100 may be calibrated according to the humidity observed by the humidity sensor 145. In this manner, photoluminescence may be determined by the receiver 125 as a function of humidity (as measured by the humidity sensor 145).

In some examples, emitted light from the laser diode 105 may be reflected off of the array of photonic silica 115 and then be captured by the receiver 125 in the third port, Port 3 130. A light filter 150 may be placed in the transmission path between the Port 2 120 and Port 3. In this manner, the receiver 125 may be adapted to receive reflected light having a predetermined wavelength (or range of wavelengths). The intensity, wavelength and/or frequency of the reflected light (filtered or unfiltered) may be interpreted as evidence of the presence of certain aromatic chemicals 140. For example, if the laser diode 105 emits a light of intensity X and frequency Y, and it is known that the array of photonic silica 115 reflects this light at intensity Z and frequency W, this intensity Z and frequency W data may indicate the presence or absence of an aromatic chemical U. In some examples, any effect of humidity and/or filtering may be taken into account.

A system 100 may include a database 155 that may be configured to store aromatic chemical information related to known intensities, wavelengths and/or frequencies associated with aromatic chemicals. For example, aromatic chemical information may indicate that chemical U corresponds to intensity Z and wavelength W, and thus an aromatic chemical (e.g., xylene) may be identified. In some embodiments, database 155 may be operably coupled to Port 2 120 and/or Port 3 130. Therefore, system 100 may be useful in identifying the presence or absence of chemicals (harmful or otherwise) in an environment where system 100 may be deployed (e.g., an aqueous environment). In some examples, Port 2 120 (comprising an array of photonic silica 115) may be configured substantially in contact with effluents, aquifers, bodies of water and/or other aqueous environments having aromatic chemicals therein. In such examples, Port 1 110 (comprising a laser diode 105) and Port 3 130 (comprising a receiver 125) may be located away (e.g., not in contact with the effluents, aquifers, bodies of water and/or other aqueous environment), yet still be configured in communication with Port 2 120. In such examples, the array of photonic silica may be exposed to (by way of the hydrophobic polymer membrane 135) the effluents, aquifers, bodies of water and/or other aqueous environments. In some examples, Port 1 110, Port 2 120 and Port 3 130 may be configured in contact with (or otherwise exposed to) the aqueous environment.

Figure 2:
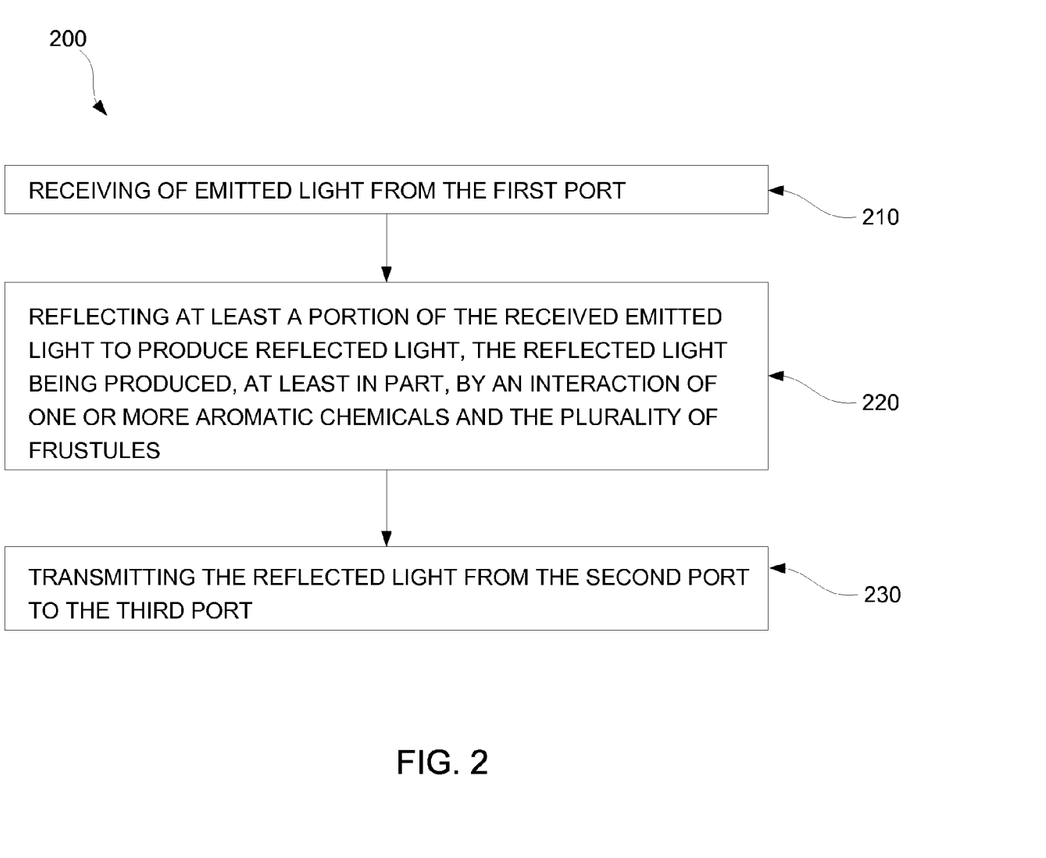
FIG. 2 is a flowchart depicting some example methods for sensing aromatic chemicals.

FIG. 2 is a flowchart depicting some example methods 200 of sensing aromatic chemicals by an optical circulator, in accordance with at least some embodiments of the present disclosure. Example method 200 may include one or more of operations, functions or actions as illustrated by blocks 210, 220 and/or 230. In method 200, an optical circulator may comprise a first port comprising a laser diode, a second port comprising an array of photonic silica comprising a plurality of frustules, and a third port comprising a receiver.

Processing may begin at block 210, which may include receiving emitted light from the first port. Block 210 may be followed by block 220. Block 220 may include reflecting at least a portion of the received emitted light to produce reflected light. Reflected light may be produced, at least in part, by an interaction of aromatic chemicals and the plurality of frustules. Block 220 may be followed by block 230. At block 230, the reflected light may be transmitted from the second port.

In some embodiments, method 200 may also include filtering the reflected light to produce filtered reflected light, and transmitting the filtered reflected light to the third port. In some other embodiments, method 200 may also include receiving the reflected light from the second port, determining the intensity, wavelength and/or frequency of the reflected light, and identifying the presence and/or absence of aromatic chemical(s). The identification of the presence and/or absence of aromatic chemical(s) may be based, at least in part, on one or more of the intensity, the wavelength and/or the frequency of the reflected light.

Figure 3:
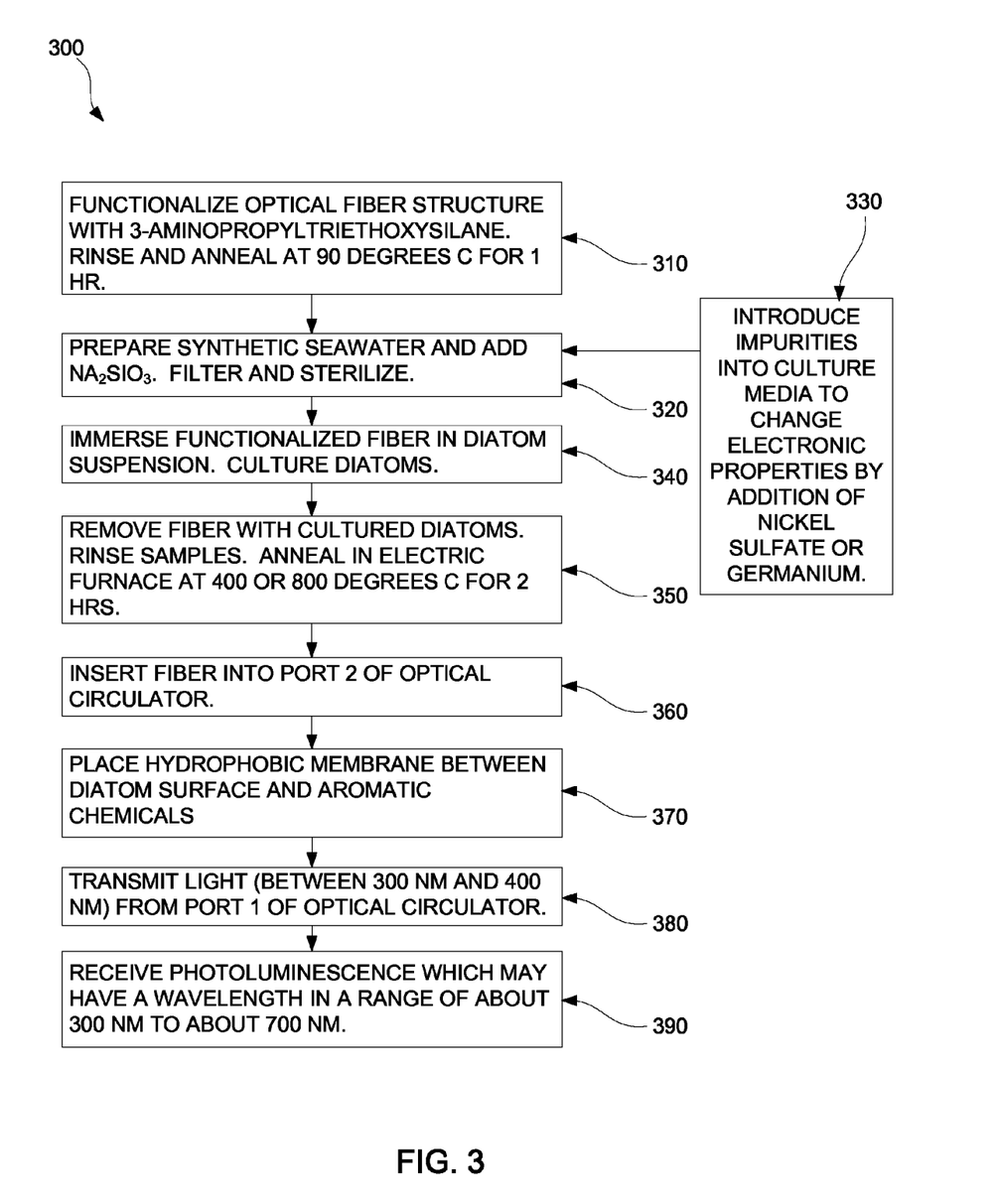
FIG. 3 is a flowchart depicting some additional example methods for sensing aromatic chemicals.

FIG. 3 is a flowchart depicting some additional example methods 300 of sensing aromatic chemicals, in accordance with at least some embodiments of the present disclosure. Example method 300 may include one or more of operations, functions or actions as depicted by blocks 310, 320, 330, 340, 350, 360, 370, 380 and/or 390.

Processing may begin at block 310, where an optical fiber may be prepared or "functionalized" such that it may be receptive to host diatoms. Block 310 may be followed by block 320 and/or block 330.

At block 320, the optical fiber may be configured to host diatoms by preparing a solution of synthetic seawater and sodium silicate (Na2SiO3) to surround the optical fiber. In some embodiments, synthetic seawater may be an aqueous solution of dissolved mineral salts and/or vitamins that is intended to simulate naturally occurring seawater.

At block 330, impurities may be introduced to the optical fiber and/or the solution surrounding the optical fiber to attain desired electronic properties. This may include adding nickel sulfate, germanium or the like. Block 330 may be followed by block 340.

At block 340, the functionalized optical fiber may be immersed in the seawater and silicate sodium silicate solution, and the diatoms may be cultured. Block 340 may be followed by block 350.

At block 350, the diatom cultured optical fiber may be removed from the solution, rinsed and annealed. In some examples, the diatoms have now been arranged into a matrix, and external frustules have been harvested. The frustules, arranged in a matrix of desired dimensions, may serve as the array of photonic silica 115 described previously with reference to FIG. 1. Block 350 may be followed by block 360.

At block 360, the optical fiber on which the frustules reside may be operably coupled with Port 2 120 of an optical circulator. Block 360 may be followed by block 370.

At block 370, a hydrophobic membrane layer may be placed between the array of photonic silica 115 and aromatic chemicals 140. Block 370 may be followed by block 380.

At block 380, light (which may have a wavelength in a range of about 300 nm to about 400 nm) may be transmitted from Port 1 110. Block 380 may be followed by block 390.

At block 390, the light hits the array of photonic silica 115, the reflected light, or photoluminescence, (which may have a wavelength in a range of about 300 nm to about 700 nm) may be received and/or captured by the receiver 125 of Port 3 130. Any observed shift in wavelength and/or intensity may be attributed, at least in part, to properties of the array of photonic silica 115 and/or environmental humidity. The present disclosure contemplates that xylene, for example, reflects light having a wavelength of approximately 557.1 nm, as compared to light reflected from air having a wavelength of approximately 533.4 nm. Also, the intensity of light reflected from xylene is greater than that of air. Similarly, pyridine reflects light at approximately 538.1 nm, as compared to light reflected from air having a wavelength of approximately 533.4 nm. Further, the intensity of light reflected from pyridine is greater than that of air. Such shifts in wavelength and/or intensity may indicate the presence and/or absence of aromatic chemicals 140 such as xylene and/or pyridine, among others.

Figure 4:
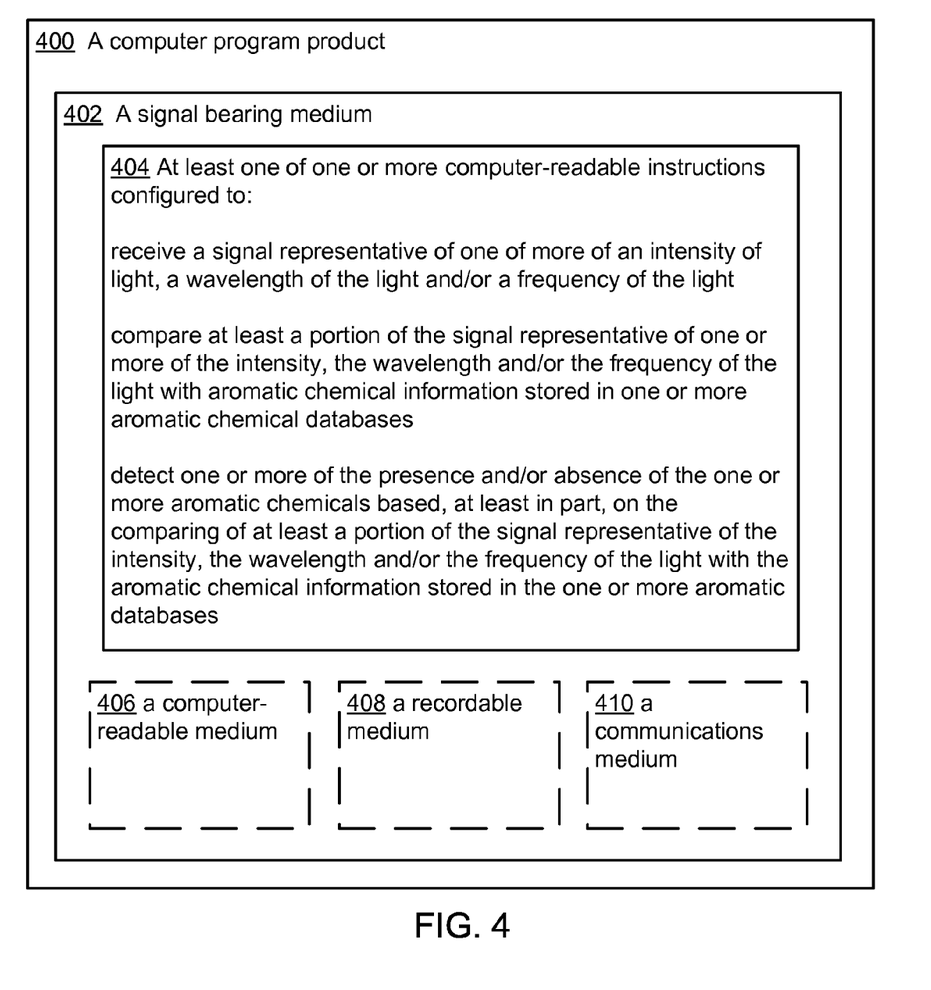
FIG. 4 is a block diagram of an example computer program product.

FIG. 4 illustrates a block diagram of an example computer program product 400 arranged in accordance with at least some embodiments described herein. In some examples, as shown in FIG. 4, computer program product 400 can include a signal bearing medium 402 that may also include machine readable instructions 404. Instructions 404 may be adapted to receive a signal representative of an intensity of light, a wavelength of the light and/or a frequency of the light. The instructions 404 may also be adapted to compare at least a portion of the signal with aromatic chemical information stored in aromatic chemical database(s). Further, instructions 404 may be adapted to detect the presence and/or absence of aromatic chemicals based, at least in part, on the comparing the signal with the aromatic chemical information stored in the aromatic database(s). In some examples, the instructions may adapted to measure and/or monitor a peak intensity and/or wavelength of the reflected light. The instructions may be further adapted to compare the peak intensity and/or wavelength of the reflected light to peak intensities and/or wavelengths of the reflected light for known chemicals. In some examples, such peak intensities and/or wavelengths of reflected light for known chemicals (e.g., those chemicals that have been characterized) may be pre-determined and stored in the aromatic chemical database(s) for look up and comparison of peak intensity and/or wavelength of the reflected light to peak intensities and/or wavelengths of reflected light for known chemicals. In this manner, the presence and/or absence of known chemicals may be determined for any known chemicals having aromatic chemical information stored in the aromatic database(s).

Also depicted in FIG. 4, in some examples, computer product 400 may include one or more of a computer readable medium 406, a recordable medium 408 and a communications medium 410. The dotted boxes around these elements depict different types of mediums included within, but not limited to, signal bearing medium 402. These types of mediums may distribute instructions 404 to be executed by logic. Computer readable medium 406 and recordable medium 408 may include, but are not limited to, a flexible disk, a hard disk drive (HDD), a Compact Disc (CD), a Digital Video Disk (DVD), a digital tape, a computer memory, etc. Communications medium 410 may include, but is not limited to, a digital and/or an analog communication medium (e.g., a fiber optic cable, a waveguide, a wired communication link, a wireless communication link, etc.).

Figure 5:
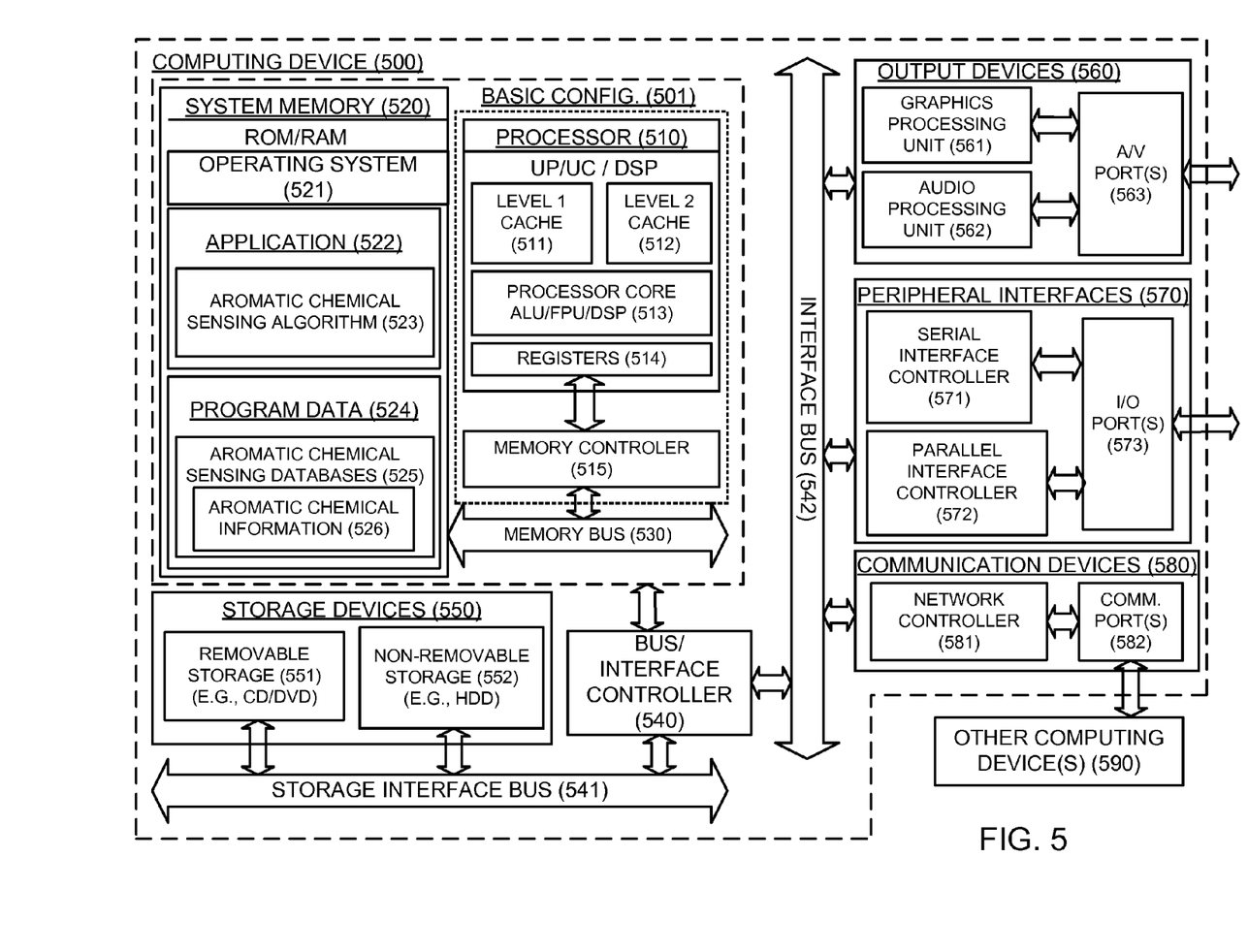
FIG. 5 is a block diagram illustrating an example computing device that may be arranged for aromatic chemical sensing implementations, all arranged in accordance with at least some embodiments of the present disclosure.

FIG. 5 is a block diagram illustrating an example computing device that may be arranged for aromatic chemical sensing implementations in accordance with at least some embodiments of the present disclosure. In a very basic configuration 501, computing device 500 typically may include one or more processors 510 and system memory 520. A memory bus 530 can be used for communicating between the processor 510 and the system memory 520.

Depending on the desired configuration, processor 510 can be of any type including but not limited to a microprocessor (µP), a microcontroller (µC), a digital signal processor (DSP), or any combination thereof. Processor 510 can include one more levels of caching, such as a level one cache 511 and a level two cache 512, a processor core 513, and registers 514. The processor core 513 can include an arithmetic logic unit (ALU), a floating point unit (FPU), a digital signal processing core (DSP Core), or any combination thereof. A memory controller 515 can also be used with the processor 510, or in some implementations the memory controller 515 can be an internal part of the processor 510.

Depending on the desired configuration, the system memory 520 can be of any type including but not limited to volatile memory (such as RAM), non-volatile memory (such as ROM, flash memory, etc.) or any combination thereof. System memory 520 typically includes an operating system 521, one or more applications 522, and program data 524. Application 522 may include an aromatic chemical sensing algorithm 523 that may be arranged to sense aromatic chemicals in aqueous environments. Program Data 524 may include one or more aromatic chemical sensing databases 525 (that may include aromatic chemical information 526) that may be useful in sensing aromatic chemicals. In some embodiments, application 522 can be arranged to operate with program data 524 on an operating system 521 such that one or more aromatic chemicals present in and/or absent from an aqueous environment may be determined and/or identified in accordance with the techniques described herein.

Computing device 500 can have additional features or functionality, and additional interfaces to facilitate communications between the basic configuration 501 and any required devices and interfaces. For example, a bus/interface controller 540 can be used to facilitate communications between the basic configuration 501 and one or more data storage devices 550 via a storage interface bus 541. The data storage devices 550 can be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 500. Any such computer storage media can be part of device 500.

Computing device 500 can also include an interface bus 542 for facilitating communication from various interface devices (e.g., output interfaces, peripheral interfaces, and communication interfaces) to the basic configuration 501 via the bus/interface controller 540. Example output devices 560 include a graphics processing unit 561 and an audio processing unit 562, which can be configured to communicate to various external devices such as a display or speakers via one or more NV ports 563. Example peripheral interfaces 570 include a serial interface controller 571 or a parallel interface controller 572, which can be configured to communicate with external devices such as input devices (e.g., keyboard, mouse, pen, voice input device, touch input device, etc.) or other peripheral devices (e.g., printer, scanner, etc.) via one or more I/O ports 573. An example communication device 580 includes a network controller 581, which can be arranged to facilitate communications with one or more other computing devices 590 over a network communication via one or more communication ports 582. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

Computing device 500 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 can also be implemented as a personal computer including both laptop computer and non-laptop computer configurations.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for sensing one or more aromatic chemicals in an aqueous environment, comprising:
    a laser diode configured to produce emitted light;
    an array of photonic silica having a plurality of frustules, the array of photonic silica being configured to receive the emitted light and reflect at least a portion of the emitted light as reflected light, wherein the reflected light adapted to be determined, at least in part, by an interaction of the one or more aromatic chemicals from the aqueous environment and the plurality of frustules; and
    a receiver configured to receive and capture at least a portion of the reflected light.

2. The system of claim 1,
    wherein the laser diode is housed in a first port, the array of photonic silica is housed in a second port and the receiver is housed in a third port; and
    wherein the first port, the second port and the third port are arranged in cooperation to operate as an optical circulator.

3. The system of claim 1, wherein the emitted light comprises a wavelength configured to yield a desired photoluminescence from the array of photonic silica.

4. The system of claim 1, wherein the emitted light comprises a wavelength in a range of about 300 nanometers to about 400 nanometers.

5. The system of claim 1, wherein the reflected light comprises a wavelength in a range of about 300 nanometers to about 700 nanometers.

6. The system of claim 1, wherein the array of photonic silica is cultured from one or more diatom.

7. The system of claim 1, wherein the plurality of frustules comprise a plurality of pores, individual pores having a diameter that may be altered upon contact with a predetermined substance.

8. The system of claim 1, wherein the predetermined substance comprises nickel sulfate.

9. The system of claim 1, further comprising an optical fiber on which the array of photonic silica is coupled.

10. The system of claim 1, wherein the one or more aromatic chemicals comprise one or more of xylene, toluene, benzene, ethylbenzene, pyridine, alcohol, tetrachloroethane and/or chlorobenzene.

11. The system of claim 1, further comprising a hydrophobic polymer membrane operably coupled to the array of photonic silica, the hydrophobic polymer membrane configured to increase a concentration of the one or more aromatic chemicals onto the array of photonic silica.

12. The system of claim 11, wherein the a hydrophobic polymer membrane comprises one or more of poly(ethylene-co-propylene), poly(acrylonitrile-co-butadiene), silicones, plasticized PVC, butadiene copolymers and/or fluoropolymer.

13. The system of claim 1, wherein the laser diode comprises one or more of an Indium Gallium Aluminum Arsenide (InGaAlAs) diode, an Indium Gallium Arsenide Phosphate (InGaAsP) diode and/or a Gallium Arsenide (GaAs) diode.

14. The system of claim 1, further comprising a light filter configured to filter the reflected light before being received by the receiver.

15. The system of claim 1, further comprising a humidity sensor operably coupled to the array of photonic silica, the humidity sensor configured to detect an amount of humidity, and further configured to provide a calibration value to the array of photonic silica based, at least in part, on the detected amount of humidity.

16. A method of sensing one or more aromatic chemicals in an aqueous environment by an optical circulator comprising a first port comprising a laser diode, a second port comprising an array of photonic silica comprising a plurality of frustules, and a third port comprising a receiver, the method comprising:
    receiving of emitted light from the first port;
    reflecting at least a portion of the received emitted light to produce reflected light, the reflected light being produced, at least in part, by an interaction of one or more aromatic chemicals in the aqueous environment and the plurality of frustules; and
    transmitting the reflected light from the second port to the third port.

17. The method of claim 16, the method further comprising:
    filtering the reflected light to produce filtered reflected light; and
    transmitting the filtered reflected light to the third port.

18. The method of claim 16, the method further comprising:
    receiving the reflected light from the second port;
    determining one or more of an intensity, a wavelength and/or a frequency of the reflected light; and
    identifying one or more of a presence and/or an absence of the one or more aromatic chemicals based, at least in part, on one or more of the intensity, the wavelength and/or the frequency of the reflected light.

19. A system for sensing one or more aromatic chemical in an aqueous environment, comprising:
- a database configured to store aromatic chemical information relating to one or more of a known frequency of the one or more aromatic chemicals, a known wavelength of the one or more aromatic chemicals and/or a known intensity of the one or more aromatic chemical;
- a laser diode configured to produce emitted light;
- an array of photonic silica having a plurality of frustules, the array of photonic silica being configured to receive the emitted light, reflect at least a portion of the emitted light as reflected light, and transmit the reflected light, wherein the reflected light is determined, at least in part, by an interaction of one or more aromatic chemicals provided about the plurality of frustules; and
- a receiver configured to:
  - receive at least a portion of the reflected light;
  - measure one or more of an intensity of the reflected light, a wavelength of the reflected light and/or a frequency of the reflected light;
  - compare one or more of the measured intensity, the measured wavelength and/or the measured frequency of the reflected light with the aromatic chemical information stored in the database; and
  - detect one or more of the presence and/or absence of the one or more aromatic chemicals based, at least in part, on the comparing of the measured intensity, the measured wavelength and/or the measured frequency of the reflected light with the aromatic chemical information stored in the database.

20. The system of claim 19,
wherein the one or more aromatic chemicals comprise one or more of xylene, toluene, benzene, ethylbenzene, pyridine, alcohol, tetrachloroethane and/or chlorobenzene; and
wherein the laser diode comprises one or more of an Indium Gallium Aluminum Arsenide (InGaAlAs) diode, an Indium Gallium Arsenide Phosphate (InGaAsP) diode and/or a Gallium Arsenide (GaAs) diode.

21. A computer program product, comprising:
a signal-bearing medium comprising computer-readable instructions stored thereon, which, when executed by one or more processing units, operatively enable a computing platform to:
- receive a signal representative of one of more of an intensity of light, a wavelength of the light and/or a frequency of the light;
- compare at least a portion of the signal representative of one or more of the intensity, the wavelength and/or the frequency of the light with aromatic chemical information stored in one or more aromatic chemical databases; and
- detect one or more of the presence and/or absence of the one or more aromatic chemicals based, at least in part, on the comparing of at least a portion of the signal representative of the intensity, the wavelength and/or the frequency of the light with the aromatic chemical information stored in the one or more aromatic databases.

22. The computer program product of claim 21, wherein the computer-readable instructions further operatively enable a computing platform to:
identify one or more of the one or more aromatic chemicals based, at least in part, on the comparing of at least a portion of the signal representative the intensity, the wavelength and/or the frequency of the light with the aromatic chemical information stored in the one or more aromatic databases.

* * * * *

UNITED STATES PATENT AND TRADEMARK OFFICE
CERTIFICATE OF CORRECTION

PATENT NO. : 8,437,965 B2
APPLICATION NO. : 12/715373
DATED : May 7, 2013
INVENTOR(S) : Sjong It is certified that error appears in the above-identified patent and that said Letters Patent is hereby corrected as shown below:

On Title Page 2, item (56), under "OTHER PUBLICATIONS", in Column 1, Line 5, delete "Joumal," and insert -- Journal, --, therefor.

In the Drawings:

In Fig. 5, Sheet 5 of 5, delete "UP/UC/DSP" and insert -- μP/ μC/DSP --, therefor.

In Fig. 5, Sheet 5 of 5, for Tag "(515)" in Line 1, delete "CONTROLER" and insert -- CONTROLLER --, therefor. (See Attached Sheet)

In the Specification:

In Column 7, Line 53, delete "NV ports" and insert -- A/V ports --, therefor.

Signed and Sealed this
Seventeenth Day of September, 2013

Teresa Stanek Rea
*Deputy Director of the United States Patent and Trademark Office*